United States Patent [19]

Whitman et al.

[11] Patent Number: 5,490,517
[45] Date of Patent: Feb. 13, 1996

[54] OCCUPANT REACH AND MOBILITY APPARATUS

[75] Inventors: Gary R. Whitman, Jamison; David A. Rose, Holland, both of Pa.

[73] Assignee: The United States of America as represented by the Secretary of the Navy, Washington, D.C.

[21] Appl. No.: 226,517

[22] Filed: Apr. 12, 1994

[51] Int. Cl.⁶ ........................................ A61B 5/00
[52] U.S. Cl. ..................... 128/774; 128/782; 33/511; 33/512
[58] Field of Search ................... 128/774, 781, 128/782; 73/172, 374.01–374.09, 865.4; 33/511, 512, 515, 514.2

[56] References Cited

U.S. PATENT DOCUMENTS

| | | | |
|---|---|---|---|
| 634,374 | 10/1899 | Stahl | 33/514.2 X |
| 2,053,810 | 9/1936 | Bisel | 33/512 X |
| 2,081,133 | 5/1937 | Bisel | 33/512 X |
| 3,693,265 | 9/1972 | Alexander et al. | 33/512 X |
| 4,603,486 | 8/1986 | Moroney et al. | 128/774 X |
| 4,742,832 | 5/1988 | Kauffman et al. | 128/782 X |
| 5,101,835 | 4/1992 | Del Re | 128/781 |

FOREIGN PATENT DOCUMENTS

| | | | |
|---|---|---|---|
| 2661600 | 11/1991 | France | 128/774 |
| 2671713 | 7/1992 | France | 128/782 |
| 91/15148 | 10/1991 | WIPO | 128/774 |
| 91/19148 | 10/1991 | WIPO | 128/774 |

*Primary Examiner*—Sam Rimell
*Attorney, Agent, or Firm*—James V. Tura; Susan E. Verona

[57] ABSTRACT

A three-dimensional grid is created by a series of panels arranged in a semi-circle about a seated subject. The panels are configured or otherwise arranged to allow the seated subject full range of reach in all directions. The subject may be seated or standing and is placed a distance from the panels. The panels include a plurality of rods which slideably project through the panels in the direction of the seated subject. To determine reach, the subject reaches toward the rods and pushes them with either hand as far away from him/her as possible. Measurements may then be taken from the end of each rod that has been moved. Similarly situated panels, including visual indicia, may be used to evaluate field of view.

8 Claims, 3 Drawing Sheets

OCCUPANT REACH AND MOBILITY APPARATUS

STATEMENT OF GOVERNMENT INTEREST

The invention described herein may be manufactured and used by or for the Government of the United States of America for Governmental purposes without the payment of any royalties thereon or therefor.

FIELD OF THE INVENTION

This invention pertains to the anatomical range of motion and visual range of seated subjects. In particular, it relates to a test device for determining occupant's reach and mobility while positioned in a workstation, i.e, aircraft crewstation, vehicle occupant compartment, factory/other workstation.

BACKGROUND OF THE INVENTION AND DESCRIPTION OF PRIOR ART

In the past, aircrew mobility and arm reach were determined by placing subjects in the crewstation or a mockup and subjectively noting their ability to reach and see various targets. This approach does not provide a quantitative assessment of reach or provide a system which would allow easy comparison among different crewstations, since results are solely related to one crewstation. Furthermore, obtaining accurate measurements is difficult within the tight confines of the crewstation if a mockup is not used. There is therefore a need for an instrument to determine aircrew mobility and arm reach to evaluate crewstation geometry and control layout, and to determine the effects of man-mounted equipment on an individual's reach and mobility.

The closest prior art patent of which the applicants are aware includes U.S. Pat. No. 4,742,832 to Kauffmann et al, issued on May 10, 1988. This patent shows the use of a frame located about a seated patient for measuring the strength of selected muscles of the human anatomy for the purpose of analyzing body symmetry. The apparatus includes a sub-frame with force-transmitting tubular members. There is no provision in the device shown in this patent for measuring the extent or angle of reach of the seated patient. Also, U.S. Pat. No. 634,374 issued to E. Stahl on Oct. 3, 1889 shows a conformator for measuring the anatomical shape of a standing person. The conformator includes a movable frame with a plurality of horizontally-extending rods slideable within the frame. When the frame is pushed against the person, the extending rods contact the person and are moved back in the direction of the frame according to the shape of the torso of person. This device is shown for use only in measuring a static-standing shape of the human figure. There is no provision for measuring hand reach or degree of movement of the person. Thus, the closest prior patent art of which the applicants are aware does not teach or suggest the invention further described herein.

SUMMARY OF THE INVENTION

The present invention overcomes the difficulties in the science for obtaining accurate quantitative measurements of a pilot's ability to reach and see various objects within the confines of a mock crewstation. As will be more fully described, the invention consists of a series of panels arranged about a seated subject. Two to five of the panels are positioned in a semi-circle around the subject, configured or otherwise arranged to approximate the location of the equipment being evaluated. The subject may be seated or standing. The panels include a plurality of rods which slideably project through the panels in the direction of the seated subject.

To determine reach, the seated subject reaches toward the rods and pushes them with either hand as far away from him/her as far as possible. Then, measurements of the distance from a fixed reference point each rod is moved may be taken and recorded. By arranging the location of the rods in horizontal rows of different height, a three-dimensional plot of reach capability may be constructed. Thus, the present invention provides an efficient method to obtain quantitative and graphic representation of the mobility and reach parameters of aircrew equipment.

Other objects, advantages and novel features of the invention will become apparent from the following detailed description of the invention when considered in conjunction with the accompanying drawings.

DESCRIPTION OF THE PREFERRED EMBODIMENT

Figure 1:
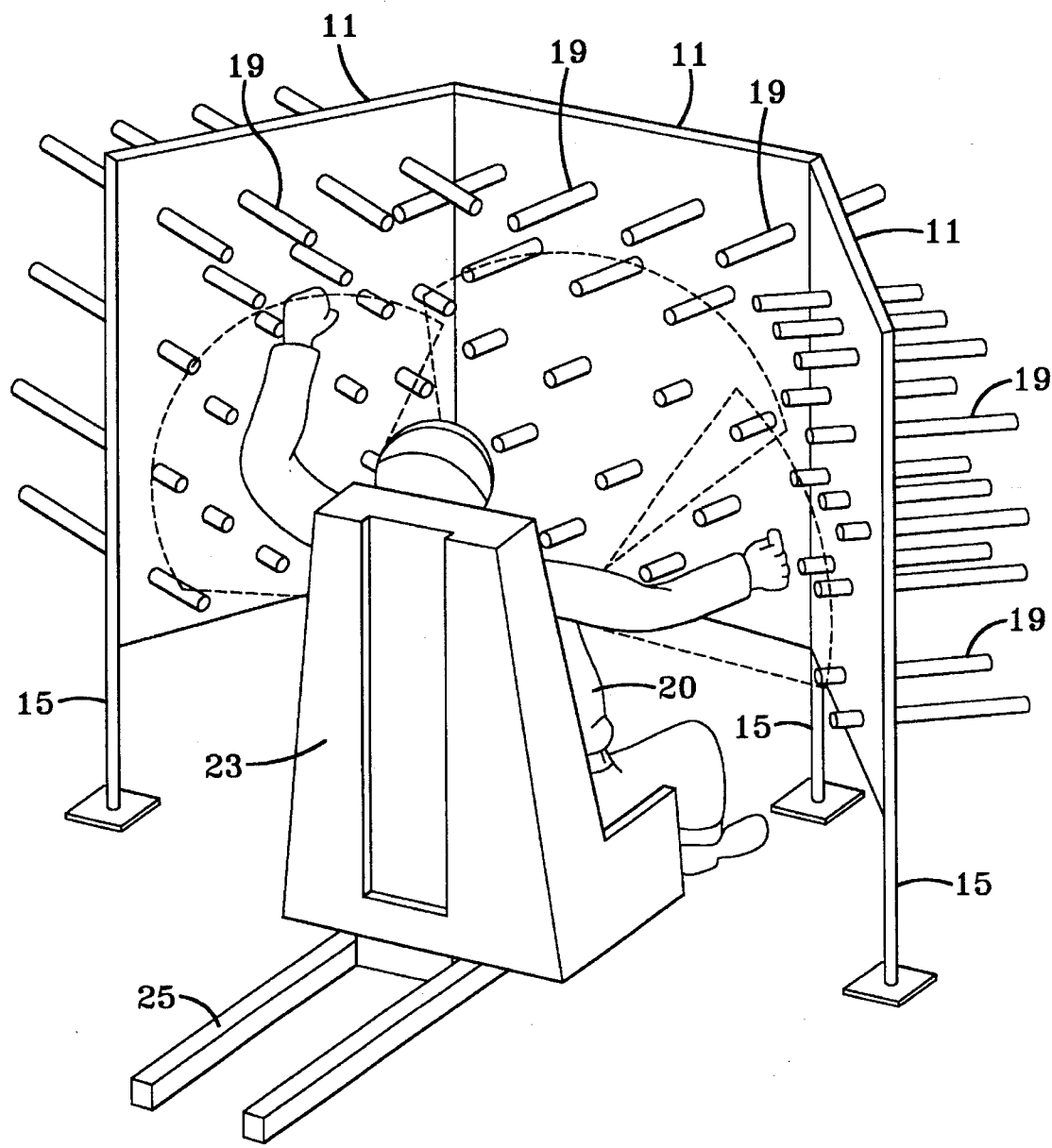
FIG. 1 is a right-side and top-rear isometric view of the present invention as shown with the maximum reach positions shown by the dotted lines.

Referring now to FIG. 1, an embodiment of the invention may be constructed by arranging a series of interconnected planar panels 11. Each panel is of suitable height, approximately 48" high and 28" to 42" wide. Each panel is approximately 5" thick and is supported by legs 15 which are approximately 24" long. The panels are drilled with an array of holes. Although individual dimensions do not form a part of the present invention, the holes may, for example, be ½" in diameter and spaced 6" apart. Metal rods 19 are inserted into each hole. The panels are positioned in a semi-circle around a subject 20 configured with any equipment being evaluated. Although the subject may be seated or standing, the subject of FIG. 1 is shown seated in a cockpit-type seat 23 slideably mounted on rails 25. The location of the seat may be adjusted by way of the rails in order to approximate the proper seat—crewstation spatial relationship and provide adequate positioning for generating reach envelope data.

Prior to taking a measurement, the rods are positioned forward through the panels within easy reach of the subject. While remaining in a comfortable seating position, the subject then pushes each rod away from him/her as far as possible with either hand. Once each rod has been repositioned by the subject, the distance from each rod's end to a fixed reference point is measured. All of the rods are pushed away from the subject and their individual positions can then be plotted in different sets of plots, one for each horizontal row of rods. These plots can then be used to compare the mobility and reach between various equipment configurations with the same subject and for different subjects. Individual plots may be made separately for right and left-hand assessment.

Figure 2:
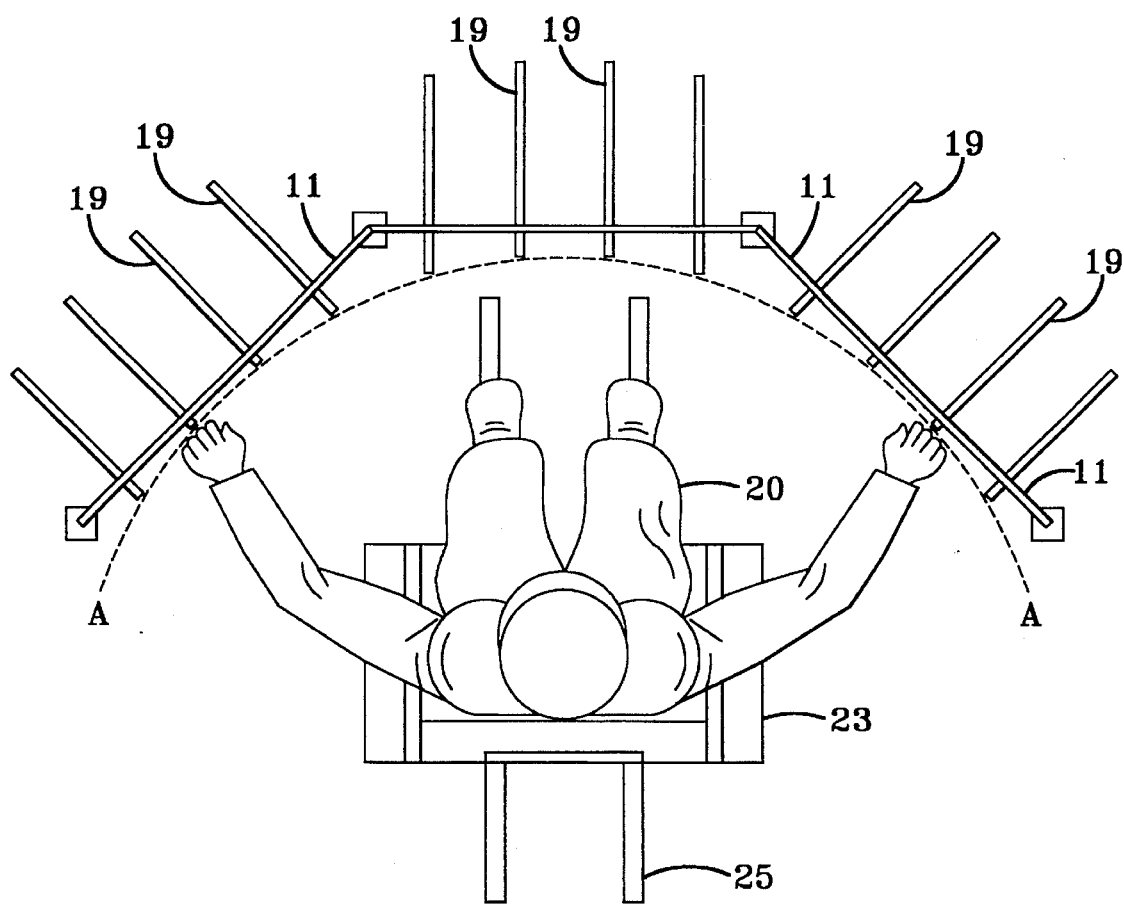
FIG. 2 is a top view taken from FIG. 1, which also shows the maximum horizontal reach depicted by a dotted line.

Referring now to FIG. 2, a top view taken from FIG. 1 shows the rods pushed back by either the right or the left hand of the seated subject represented by arc A, which is defined by the ends of the rods.

Although the choice of materials is not a necessary part of the present invention, the preferred embodiment utilizes wood as the construction material for the panels and a suitable metal, such as steel or aluminum, for the rods. The panel construction could also be made of light-weight materials, such as aluminum frames supporting fiber-board sheets. Also, for taking accurate measurements, the subject is preferably dressed in the appropriate clothing configuration to simulate the actual operational condition. To determine the effect of flight clothing upon hand and arm mobility, reach assessments can also be measured for different clothing configurations.

Figure 3:
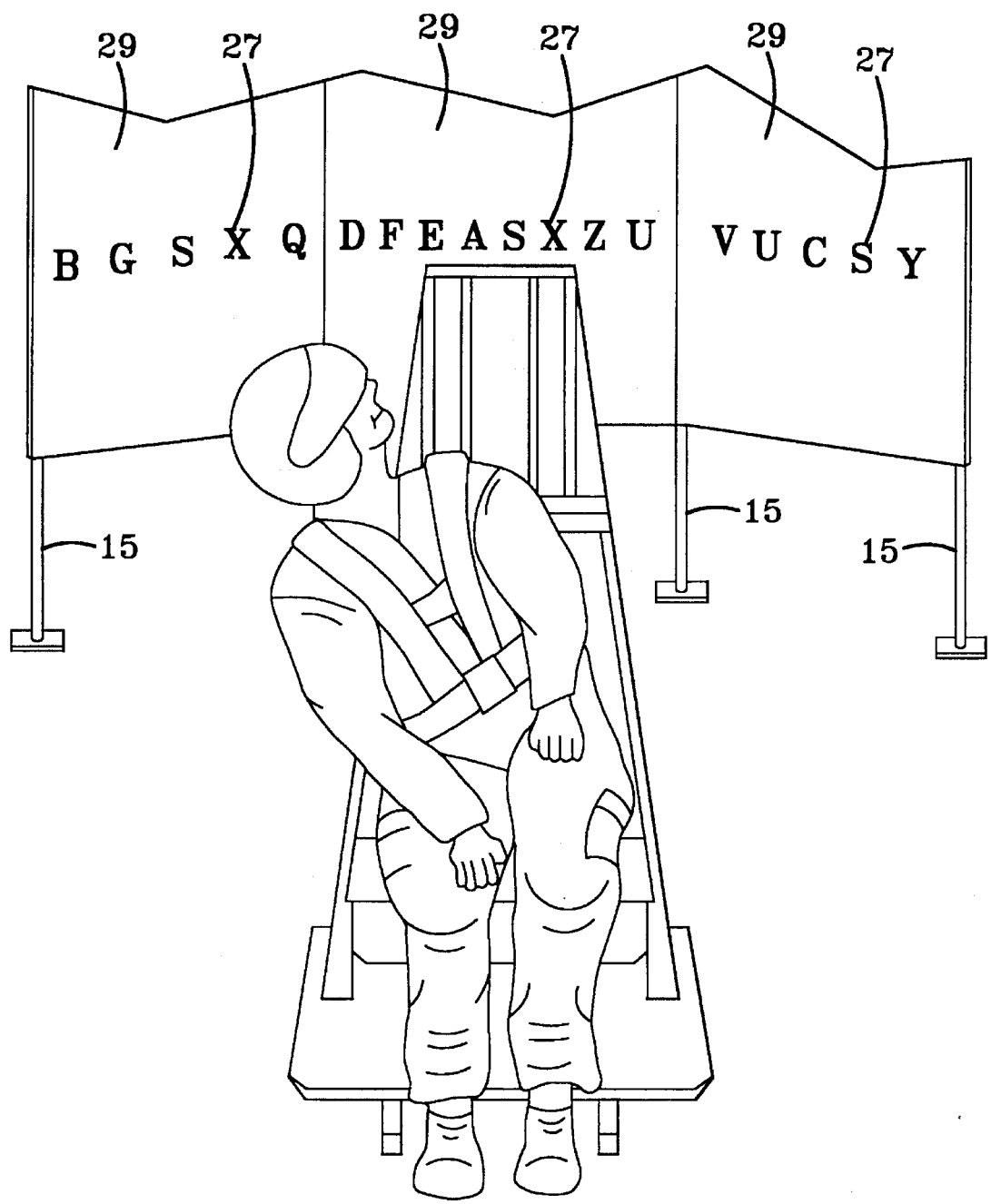
FIG. 3 is a front isometric view showing an alternate embodiment of the present invention employed to measure a rearward field of view.

Referring now to FIG. 3, an additional embodiment of the present invention is shown using panels similar to those constructed as above-described with regard to FIGS. 1 and 2, but placed behind the seated subject, rather than in front. In this embodiment, the panels are not fitted with rods, but rather include printed indicia, such as letters of the alphabet 27. The panels 29 are arranged in a semi-circle behind the seated subject and by turning his/her head and reporting the letters that can be sighted, the range of the subject's rearward vision may be measured. The angle between the indicia viewed and the seat may then be measured to translate the range of vision to the actual crewstation.

Three panels whose widths total 116 inches are, arranged in a semi-circle a distance of 84 inches from the eye position of a seated subject, with the seated subject facing away from the panels, such that an arc of approximately 80 degrees is formed by the panel at a radius of 84 inches. The panels are affixed with alphanumeric characters 4 inches in height at a height identical to the eye position of the seated subject. Each character equates to a particular field of view measurement. The characters are affixed in a continuous line across the three panels. Larger arcs can be used by varying the panel configuration.

As shown by the above description of the preferred embodiment, the present invention overcomes the deficiencies of the prior art. The data obtained by the quantitative and graphic representation of the mobility and reach of aircrew allows a direct comparison among various configurations and their effects on reach, mobility and field of view. It can also lend itself for use in computer-aided design, both for aircrew equipment and crewstation design. Data acquired from this invention can also be used to generate requirements for aircrew equipment. In another application, this device can also be used in automotive and other general personnel workstation design, test or evaluation.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. An aircrew field of view measurement device for evaluating a subject's crew person rearward vision related to equipment located within actual cockpit structures each having known dimensions and each having a rearward structure and an aircraft cockpit located therein, said measurement device comprising:

a plurality of vertical panels each located a predetermined distance behind said subject crew person and arranged in a semi-circle, the predetermined distances between said subject and said panels approximating the distances between said subject and said equipment within said actual cockpit structures; and a plurality of indicia on said panels, said indicia being arranged along a horizontal line across each of said panels and being sighted by said subject crew person turning his/her head so that said indicia is within said subject's crew person rearward vision.

2. The measurement device of claim 1, further including a seat for said subject crew person, said seat being positioned in front of said panels and facing away from said panels, said seat being located a distance from each of said panels which approximates the distance between said aircraft cockpit seat and said rearward cockpit structure.

3. The measurement device of claim 2, wherein said seat is movable between positions closer to and farther from said panels.

4. The measurement device of claim 3, wherein said panels are located in a semi-circle about said seated subject.

5. The measurement device of claim 4, wherein said panels are free-standing and supported by legs.

6. The measurement device of claim 3, wherein said seat is slideably affixed to rails.

7. The method of measuring aircraew reach capability relative to a fixed point, comprising the steps of:

placing a plurality of vertically standing panels arranged in a semi-circle in front of a subject;

placing a plurality of horizontally extending rods through said panels in the direction of said subject to points within an extent of said subject's reach which involves little difficulty to achieve;

pushing the ends of said rods toward said panels by said subject which involves the full extent of said subject's reach to achieve; and measuring the distance the ends of said rods extend from said fixed point.

8. The method of measuring aircrew reach capability relative to a fixed point of claim 7, wherein said rids are arranged along a plurality of horizontal rows each of a different height.

\* \* \* \* \*